United States Patent [19]

Haupt

[11] Patent Number: 5,252,715
[45] Date of Patent: Oct. 12, 1993

[54] PROCESS FOR THE PREPARATION OF A PASTEURIZED AND IRON-FREE HUMAN TRANSFERRIN AND THE USE THEREOF

[75] Inventor: Heinz Haupt, Marburg, Fed. Rep. of Germany

[73] Assignee: Behringwerke Aktiengesellschaft, Marburg, Fed. Rep. of Germany

[21] Appl. No.: 804,927

[22] Filed: Dec. 11, 1991

[30] Foreign Application Priority Data

Dec. 13, 1990 [DE] Fed. Rep. of Germany ....... 4039721

[51] Int. Cl.$^5$ .............................................. C07K 3/00
[52] U.S. Cl. .................................... 530/394; 530/350; 530/395; 530/400; 530/413
[58] Field of Search ................... 424/92; 530/350, 395, 530/400, 413, 380, 394, 412, 417

[56] References Cited

U.S. PATENT DOCUMENTS

| | | | |
|---|---|---|---|
| 4,440,679 | 4/1984 | Fernandes et al. | 530/363 |
| 4,623,717 | 11/1986 | Fernandes et al. | 530/380 |
| 4,841,026 | 6/1989 | Van Beveren et al. | 530/418 |
| 5,041,537 | 8/1991 | Bethke et al. | 530/394 |

*Primary Examiner*—Howard E. Schain
*Assistant Examiner*—P. Lynn Touzeau
*Attorney, Agent, or Firm*—Finnegan, Henderson, Farabow, Garrett & Dunner

[57] ABSTRACT

A process for the preparation of an iron-free, pasteurized human transferrin is described and entails human transferrin being pasteurized in the presence of a complexing agent in solution, and the complexing agent being removed with the bound iron.

This transferrin can be used as pharmaceutical or growth factor.

2 Claims, No Drawings

PROCESS FOR THE PREPARATION OF A PASTEURIZED AND IRON-FREE HUMAN TRANSFERRIN AND THE USE THEREOF

DESCRIPTION

The invention relates to a process for the preparation of a pasteurized and iron-free human transferrin and to the use thereof.

Transferrin is the transport protein for iron in the blood plasma of vertebrates, including humans.

Human transferrin is mainly used as growth factor for cell cultures, for example for growing mammalian cells in genetic engineering and as therapeutic in the rare cases of atransferrin anemia.

Various processes for the preparation of human transferrin from serum or plasma have been described and make use of a wide variety of fractionation principles and can be carried out on the industrial scale, for example by stepwise precipitation using ethanol/water mixtures in the cold, resulting in transferrin in crystalline form, by precipitation with ethyl alcohol in the presence of calcium and zinc ions, and by adsorption of impurities onto carboxymethyl- and DEAE-cellulose, resulting in pasteurized, iron-saturated transferrin which can be used therapeutically, by fractional salting-out using ammonium sulfate and adsorption of impurities onto aluminum hydroxide in aqueous medium, using a combined Rivanol/alcohol process, in which case human transferrin with a purity of at least 85% was isolated and was able subsequently to be crystallized in pure form with good yields without difficulty, and by means of a combination of precipitation steps with Rivanol and ammonium sulfate and adsorption of impurities on aluminum hydroxide.

Besides these purification processes suitable for the industrial isolation of human transferrin, the literature describes various other methods tailored to the preparation of small amounts of transferrin for research purposes.

Although human transferrin is, like all plasma products, nowadays exclusively prepared from HBsAg-negative and anti-HIV-negative plasma and is to be categorized in the group of low-risk products in terms of the transmission of viral diseases on the basis of the preparation process and after years of clinical use, it is not possible to rule out a residual risk of viral contamination. It therefore appeared desirable, besides the virus elimination already in existence, to combine an additional efficient virus-inactivating step with the preparation process in order to achieve the currently highest possible safety standard.

Essentially three processes are known for the sterilization of plasma proteins: heat treatment in liquid or dry state; combined treatment with $\beta$-propiolactone and UV light irradiation and treatment with ether or tri-n-butyl phosphate in combination with detergents.

Iron-saturated transferrin can be pasteurized at 60° C. for 10 hours in solution, whereas apotransferrin is denatured under thes conditions.

All these processes have the disadvantage, in respect of the preparation of an iron-free transferrin product, that it is necessary to follow the sterilization by a separate step to remove iron which has been added or is naturally bound to transferrin with the aid of a complexing agent (usually EDTA).

The object of the present invention is to provide a process which makes it possible simultaneously to remove and complex the transferrin-bound iron and to stabilize the formed apotransferrin during the process of heating at 60° C. for 10 hours.

It was known to use complexing agents as stabilizers during the pasteurization of C1 inactivator, alpha$_1$-antitrypsin or certain coagulation factors, but it was not at all predictable that the biological activity of apotransferrin would also be retained on sterilization in the presence of such compounds.

The invention relates to a process for the pasteurization of human transferrin, which comprises pasteurizing a solution of human transferrin which contains a complexing agent.

It is possible for this purpose to add sufficient complexing agent, preferably a soluble citrate or a salt of ethylenediaminetetraacetic acid (EDTA), to result in a concentration of at least 0.4 mol/l, preferably 1.2M sodium citrate or 0.5M EDTA, to a solution which has been prepurified by known methods and contains 10-100 g, preferably 40-60 g, of transferrin per l, to adjust the pH, preferably with citric acid, to 7-8, and to keep the mixture at 60° C. for 10 hours.

Whereas the formed apotransferrin is protected from thermal inactivation under these conditions, model viruses experimentally added in this process are inactivated after only short incubation times.

As proof, samples of human transferrin (5% in 1.2M citrate pH 7.5) were mixed in the ratio 10:1 with HSV-1, poliovirus type 1 or vacciniavirus. These samples were heated at 60° C. in a temperature-controlled water bath in time intervals up to 10 hours. Samples were removed after 30 minutes, 1, 2, 4, 6, 8 and 10 hours and immediately titrated for their virus content. The titration of herpes simplex virus and vacciniavirus took place on vero cells, and that of poliovirus on HEP-2 cells, with eight parallel cultures per virus dilution stage in each case. If no infectious virus was detected in a titration of this type (lower detection limit 1.5 log ID$_{50}$/ml), a volume corresponding to 1 ml of original sample was tested in duplicate in separate culture bottles. If all the test cultures remained negative, the virus titer was stated at $\leq$10 ID$_{50}$/ml. The titers were calculated by the method of Reed and Muench.

Results: (all titers stated as log 10 ID$_{50}$/ml)

HSV-1: Virus titer in the transferrin/virus mixture 6.4 before inactivation. No infectious virus detectable after an inactivation time of 1 hour.

Poliovirus: Virus titer in the transferrin/virus mixture 5.7. No infectious virus detectable after an inactivation time of 30 minutes.

Vacciniavirus: Virus titer in the transferrin/virus mixture 6.5. No remaining infectious virus detectable after an inactivation time of 2 hours.

The short inactivation times which sufficed for complete inactivation of the three model viruses show that very efficient inactivation of naked, enveloped and complex viruses is possible by pasteurization of transferrin. HSV-1 can be regarded as a model of the large group of viruses surrounded by a lipid-containing envelope and is distinguished in this group by having relatively high stability. Retroviruses, such as the HIV viruses, are more rapidly inactivated than HSV in all cases investigated to date. Poliovirus and vacciniavirus are representatives of naked viruses which are known to have considerably higher stability to heat. Despite their high stability, even these two model viruses are inactivated unexpectedly rapidly. The pasteurization of transferrin is thus a very efficient method for the inactivation of enveloped and naked viruses of various species.

Heating in the presence of a complexing agent simultaneously results in the complexing of the iron which is naturally present in transferrin, and which can be washed out during the subsequent purification, for example by ultrafiltration.

It has proven beneficial to incorporate pasteurization in the preparation process before the last purification step. At this stage of working up, the transferrin already has sufficiently high purity, and this procedure has the advantage that the residual amounts of protein impurities, which are usually denatured during the heating process, are easier to remove by the subsequent adsorption, for example on aluminum hydroxide. Small quantities of aggregated transferrin are likewise removed by the adsorption.

It is possible in combination with purification processes known for transferrin to obtain by the described process from Cohn fraction IV a pasteurized, iron-free human transferrin with an immunochemical purity of at least 98%. The resulting solution of pasteurized, iron-free transferrin can undergo subsequent purification and concentration, sterilization by filtration and lyophilization in a known manner. The quantity of aggregates (dimers) is about 2-5% which is of the same order as in a lyophilized, non-pasteurized product.

The iron-binding capacity of the pasteurized transferrin is completely retained. The crystallization of iron-free and iron-saturated transferrin after the pasteurization process takes place, using ethyl alcohol or polyethylene glycol, with the same ease and in the same crystal forms as with non-pasteurized transferrin. Finally, the property of the pasteurized transferrin of acting as growth factor in cell cultures is likewise completely retained.

EXAMPLE 1

1,000 g of crude transferrin dry material which has been prepurified by known methods and has an immunological purity of about 90% and an iron content of 550 μg/g of protein are dissolved in distilled water, and sufficient trisodium citrate is added to produce 20 l of an approximately 5% strength protein solution containing 1.2M trisodium citrate. The pH of the solution is adjusted to 7.5 with 1M citric acid.

The crude transferrin solution is heated to 60° C. in a water bath while stirring continuously and kept at 60° C. for 10 hours. After cooling to room temperature, a slight turbidity produced during the heating process is removed by clarifying filtration.

The sodium citrate and the iron bound thereto are washed out of the protein solution with distilled water by ultrafiltration (membrane exclusion limit = 10 KD). The iron content of the transferrin solution is now less than 20 μg/g of protein.

The final purification of the iron-free transferrin which now takes place is carried out by known methods such as adsorption of the residual impurities on aluminum hydroxide or by chromatography on anion exchangers.

EXAMPLE 2

The initial procedure is as in Example 1; however, ethylenedinitrilotetraacetic acid disodium salt is used, in place of trisodium citrate, in a concentration of 0.5M.

The pH of the solution is adjusted to pH 7.5 with 1N sodium hydroxide solution. Subsequent treatment is carried out as described in Example 1.

I claim:

1. A process for preparing pasteurized and iron-free human transferrin, comprising pasteurizing a solution containing human transferrin and a complexing agent that binds iron, and then removing the complexing agent and the iron bound thereto from the transferrin.

2. The process as claimed in claim 1, wherein a soluble citrate or a salt of ethylenediaminetetraacetic acid (EDTA) is used as complexing agent.

* * * * *